United States Patent [19]

Boot

[11] Patent Number: 4,501,923
[45] Date of Patent: Feb. 26, 1985

[54] PROCESS FOR PREPARING ADRENOCHROME

[75] Inventor: Deryck F. Boot, Knighton, England

[73] Assignee: Minnesota Mining and Manufacturing Company, St. Paul, Minn.

[21] Appl. No.: 417,608

[22] Filed: Sep. 13, 1982

[30] Foreign Application Priority Data

Sep. 21, 1981 [GB] United Kingdom ............... 8128457

[51] Int. Cl.³ ........................................... C07D 209/36
[52] U.S. Cl. .................................................. 548/484
[58] Field of Search ......................................... 548/484

[56] References Cited

U.S. PATENT DOCUMENTS 3,708,431  1/1973  Prussin .................................. 424/73
4,010,872  3/1977  Lozano ................................. 424/73

FOREIGN PATENT DOCUMENTS 1519756  8/1978  United Kingdom ................ 548/484

OTHER PUBLICATIONS

Seiyama, et al., "Oxidative Dehydroaromatization", *J. of Catalysis*, vol. 24, pp. 76–81, (1972).
Nakajima, et al., "Adrenochrome Derivatives", *Chem. Abst.*, 88: 89518n, (1977).
Wellman, et al., "Indirect Electrochemical Processes", *Chem. Abst.*, 88: 29563(p), (1978).
Perumal, et al., "Oxidation of Aromatic Substrates", *Chem. Abst.*, 92: 198135(p), (1979).
Marsheck, Robt., "Cyclic Oxidative Dehydrogenation . . .", *Chem. Abst.*, 95: 42321(x), (1981).

*Primary Examiner*—Donald G. Daus
*Assistant Examiner*—G. Hendricks
*Attorney, Agent, or Firm*—Donald M. Sell; James A. Smith; Carolyn A. Bates

[57] ABSTRACT

A process is described for preparing adrenochrome comprising oxidizing adrenaline or a salt thereof with a persulfate in an aqueous medium at a pH in the range 4 to 8 in the presence of one or more water-soluble salts of bismuth.

9 Claims, No Drawings

PROCESS FOR PREPARING ADRENOCHROME

This invention relates to a process for preparing adrenochrome, and in particular to the preparation of high quality adrenochrome by oxidation of adrenaline.

Adrenochrome is an intermediate for adrenochrome monosemicarbazone and adrenochrome monoaminoguanidine known as hemostatics. Adrenochrome has been commercially prepared by oxidizing adrenaline or its salts with potassium ferricyanide in an aqueous medium. This process is uneconomical in view of the large quantities of potassium ferricyanide needed and the ensuing effluent disposal problems, together with variability in product quality. It is reported in the literature that persulfates can be employed as the oxidizing agent. The use of the persulfates is advantageous since the problems associated with the use of potassium ferricyanide are precluded and they are significantly cheaper than potassium ferricyanide. However, the oxidation process with persulfates is slow so that long reaction periods are required for complete reaction. This is disadvantageous in operation efficiency of a process. Also, this results in lowering of yields of adrenochrome since the produced adrenochrome may be further oxidized to decompose to black by-products during the reaction. Accordingly, oxidation with persulfates is not practical for the commercial manufacture of adrenochrome.

British Patent Specification No. 1,519,756 discloses a process for preparing adrenochrome by oxidizing adrenaline or a salt thereof with a persulfate in the presence of a water-soluble salt of copper, zinc, nickel or cobalt. The presence of these catalysts provides a high reaction rate and a good yield of high quality adrenochrome.

We have now found a further range of catalysts which are effective in catalysing the oxidation of adrenaline with a persulfate.

According to the present invention, there is provided a process for preparing adrenochrome which comprises oxidizing adrenaline or a salt thereof with a persulfate in an aqueous medium at a pH in the range 4 to 8 in the presence of one or more water-soluble salts of bismuth.

Bismuth salts are not particularly soluble in water but their solubilities are adequate in the quantities employed in the process of the invention.

The presence of water-soluble salts of bismuth accelerates the oxidation reaction resulting in high quality adrenochrome in high yields. Any water-soluble salt of bismuth can be employed in the present invention although the nitrate and oxynitrate salts are preferred. Other suitable bismuth salts include bismuth oxycarbonate and bismuth citrate.

Suitable persulfates for use in the present invention include potassium persulfate, sodium persulfate and ammonium persulfate. Sodium and ammonium persulfates are preferred in view of their good solubility in water.

The aqueous reaction medium is maintained at a pH from 4 to 8. Preferably a buffer is present, e.g., sodium hydrogencarbonate, sodium dihydrogenphosphate, disodium hydrogenphosphate, potassium acetate and sodium acetate. Sodium hydrogencarbonate is preferred.

The oxidation reaction of adrenaline with the persulfate is conducted in an aqueous medium at pH 4 to 8 in the presence of one or more water-soluble bismuth salts. Generally, a uniform aqueous solution of adrenaline is first prepared by adding an acid such as hydrochloric acid to an aqueous dispersion of adrenaline, or by directly dissolving a salt of adrenaline in water. The aqueous solution is then added to a separately prepared aqueous medium containing the persulfate, the bismuth catalyst and the buffer.

The water-soluble bismuth salt may be employed in an amount of from 0.001 to 0.01 mole, preferably 0.005 to 0.01 mole, per mole of adrenaline. Amounts of the bismuth salts less than 0.001 mole do not significantly increase the reaction rate. Amounts of the bismuth salt in excess of 0.01 mole may lead to excessive oxidation causing decomposition of the produced adrenochrome and the formation of tar-like by-products.

The persulfate is generally used in an amount in the range 2.0 to 2.5 mole per mole of adrenaline. A buffer is generally used in an amount of from 4 to 7 moles, preferably 5 to 6 moles, per mole of adrenaline.

The reaction is generally carried out at $-5°$ C. to $15°$ C., preferably $0°$ to $5°$ C. With the progress of the reaction, the reaction mixture is tinged with purplish red due to the production of adrenochrome and its color becomes deeper with increasing adrenochrome content. The reaction is continued until the absorbance at a wavelength of 495 nm, which is measured by sampling the reaction mixture at an appropriate time during the reaction, reaches the maximum. Thus, the further oxidation of the product adrenochrome can be minimized and adrenochrome can be obtained in the maximum yield. The reaction time required for the maximum yield generally varies in the range of 30 to 45 minutes, depending on the temperature of the reaction mixture and the level of catalyst employed. Thus, adrenochrome can be obtained in maximum yields in a very short period of time.

After completion of the reaction, adrenochrome is obtained as a solution. Adrenochrome is very unstable due to its ortho-quinoid structure and, therefore, is usually stabilized by conventional derivation with hydrazines, e.g., aminoguanidine, semicarbazide, phenylhydrazine, o-nitrophenylhydrazine, p-nitro phenylhydrazine and 2,4-dinitrophenylhydrazine.

Adrenochrome monoaminoguanidine and adrenochrome monosemicarbazone are useful as hemostatics and these hydrazine derivatives serve both for stabilization of adrenochrome and the preparation of useful medicines. Adrenochrome monoaminoguanidine and adrenochrome monosemicarbazone obtained utilizing the process of the present invention are far less colored than those prepared by the method using potassium ferricyanide.

The stabilization of adrenochrome by formation of the hydrazine derivative and the isolation of the product may be conducted by the following technique. The hydrazine compound, e.g., semicarbazide or aminoguanidine, is added to the reaction mixture containing the adrenochrome produced by the process of the invention. The hydrazine compound is generally dissolved in water in the form of the hydrochloride or sulfate and is added to the reaction mixture in one or more portions. The amount of hydrazine compound added is generally within the range 1.0 to 1.25 moles per mole of adrenochrome. The stabilization treatment is generally conducted for 30 minutes to 3 hours at a temperature of $0°$ to $15°$ C. The stabilization is preferably carried out at pH 2 to 5 when the hydrazine is monoaminoguanidine or pH 5 to 7 when the hydrazine is semicarbazide. The optimum pH for the semicarbazide stabilization is conveniently achieved by adding a suitable buffer to the semicarbazide solution prior to its addition to the adrenochrome solution. Suitable buffer salts include those previously listed. Potassium acetate is the preferred buffer and the amount employed is usually within the range 1.5 to 2.5 mole per mole of semicarbazide.

After the completion of the stabilization, the derivative of adrenochrome is isolated from the reaction mixture by separating the precipitate in a normal manner, e.g., filtration, followed by washing. The derivative of adrenochrome is obtained in the form of powder. Prior to the separation, the treated reaction mixture may be neutralized with an alkali, e.g., sodium hydroxide, to precipitate the dissolved adrenochrome derivative. The isolated powders may be purified in the usual manner such as active carbon treatment, chelate treatment and recrystallization.

The invention will now be illustrated by the following Examples.

EXAMPLE 1

To a 3-liter beaker was charged distilled water (1000 ml), ammonium persulfate (95.8 g; 0.42 mole) and sodium hydrogencarbonate (93 g; 1.1 mole). The mixture was stirred and cooled to 0° C. To this solution was added a solution of bismuth nitrate pentahydrate, Bi($NO_3$)$_3$.5$H_2O$, (0.97 g; 0.002 mole dissolved in 25 ml 10% HCl). This was followed by the dropwise addition of an aqueous solution of adrenaline hydrochloride (44.0 g; 0.2 mole) dissolved in water (100 ml) over 20 minutes at 0° to 5° C. followed by a period of stirring for 30 minutes at 0° to 5° C. During the reaction, a part of the reaction mixture (1 gm) was taken out and was diluted with water to 1000 ml and the absorbance of the dilute solution was measured at a wavelength of 495 nm. The absorbance increased to a maximum after 30 to 45 minutes.

To the resulting adrenochrome solution was added a solution of semicarbazide hydrochloride (23.6 g; 0.212 mole) and potassium acetate (41.2 g; 0.42 mole) dissolved in water (150 ml), over 15 minutes at below 10° C.

The reaction was stirred for a further 2 hours to allow the product to crystallize. The product was collected by filtration, washed with water and dried to give 40.0 g crude powder of adrenochrome monosemicarbazone. Purification of the adrenochrome monosemicarbazone was achieved by suspending the solid in water (25 volumes) and treating with an excess of sodium hydroxide to afford a solution. After active carbon treatment and addition of ethylenediamine tetraacetic acid the purified product was precipitated by the addition of acetic acid to pH 5.5. The adrenochrome monosemicarbazone was isolated in the conventional manner.

The infra-red absorption spectrum and ultraviolet absorption spectrum of the purified adrenochrome monosemicarbazone were measured. The infra-red absorption spectrum showed the characteristic absorptions at 3350, 3190, 1700, 1660, 1560, 1410, 1295, 1195, 1095, 1060, 810 and 560 cm$^{-1}$. The ultra-violet absorption spectrum of the purified powder showed maximum absorption at 354 nm. The melting point, infra-red absorption spectrum and ultra-violet absorption spectrum agreed with those of the authentic adrenchrome monosemicarbazone, and the reaction product was identified as adrenochrome monosemicarbazone.

EXAMPLE 2

Adrenochrome was prepared in the same manner as in Example 1. To the resulting adrenochrome solution was added an aqueous solution of aminoguanidine hydrochloride (23.4 g; 0.212 mole) dissolved in water (100 ml) at below 5° C., the pH of the resulting solution was adjusted to 2.9 with dilute HCl and stirred for a further 30 minutes at below 15° C., during which time a deep orange solid precipitated. The pH was further adjusted with dilute sodium hydroxide solution to a final pH of 9.0 to 10.0. The resulting yellow orange slurry was then stirred for a further 15 minutes. The product was isolated by filtration, washed and dried to give 41.0 g crude powder of adrenochrome monoaminoguanidine. The crude powder was dissolved in a 5% by weight aqueous solution of sulfurous acid, and after active carbon treatment, a small quantity of ethylene diaminetetraacetic acid was added. Four percent by weight aqueous solution of sodium hydroxide was then added, and the precipitate was separated and washed to give purified adrenochrome monoaminoguanidine. The infra-red absorption spectrum and ultra-violet absorption spectrum of the purified adrenochrome monoaminoguanidine were measured. The infra-red absorption spectrum showed the characteristic absorptions at 3330, 3170, 1640, 1590, 1500, 1395, 1365, 1330, 1295, 1150, 1070, 860, 815 and 720 cm$^{-1}$. The ultra-violet spectrum showed the maxima absorption of 348 nm and 445 nm. The infra-red absorption spectrum, ultra-violet absorption spectrum and the melting point agreed with those of an authentic adrenochrome monoaminoguanidine, and the formation of the desired product was thus confirmed.

EXAMPLE 3

To a 3-liter beaker was charged distilled water (1000 ml), ammonium persulfate (95.8 g; 0.42 mole) and sodium hydrogencarbonate (93 g; 1.1 mole). The mixture was stirred and cooled to 0° C. To this solution was added a solution of bismuth oxycarbonate (BiO)$_2$CO$_3$ (0.5 g; 0.001 mole dissolved in 25 ml 10% HCl). This was followed by the dropwise addition of an aqueous solution of adrenaline hydrochloride (44.0 g; 0.2 mole) dissolved in water (100 ml) over 20 minutes at 0° to 5° C. followed by a period of stirring for 30 minutes at 0° to 5° C.

To the resulting adrenochrome solution was added a solution of semicarbazide hydrochloride (23.6 g; 0.212 mole) and potassium acetate (41.2 g; 0.42 mole) dissolved in water (150 ml), over 15 minutes at below 10° C. The reaction was stirred for a further 2 hours to allow the product to crystallize. The product was collected by filtration, washed with water and dried to give 38.3 g crude powder of adrenochrome monosemicarbazone which slowed the characteristic absorptions of 3350, 3190, 1700, 1660, 1560, 1410, 1295, 1195, 1095, 1060, 810 and 560 cm$^{-1}$. The ultra-violet absorption spectrum showed a maximum at 354 nm. The infra-red absorption spectrum and ultra-violet absorption spectrum agreed with those of an authentic sample of adrenochrome monosemicarbazone.

EXAMPLE 4

The procedure of Example 3 was repeated except the bismuth oxycarbonate was replaced with bismuth citrate $C_6H_5BiO_7$ (0.78 g; 0.002 mole). Similar results to those obtained in Example 3 were obtained.

What I claim is:

1. A process for preparing adrenochrome which comprises oxidizing adrenaline or a salt thereof with a persulfate in an aqueous medium at a pH in the range 4 to 8 in the presence of one or more water-soluble salts of bismuth.

2. The process according to claim 1 wherein said water-soluble salt of bismuth is selected from the group consisting of bismuth nitrate, bismuth oxynitrate, bismuth oxycarbonate and bismuth citrate.

3. The process according to claims 1 or 2 wherein said water-soluble salt of bismuth is used in an amount in the range 0.001 to 0.01 mole per mole of adrenaline.

4. The process according to claim 3 wherein said water-soluble bismuth salt is used in an amount in the range of 0.005 to 0.01 mole per mole of adrenaline.

5. The process according to claims 1 or 2 wherein said aqueous medium includes a buffer in an amount of from 4 to 7 moles per mole of adrenaline.

6. The process according to claim 5 wherein said buffer is present in an amount of from 5 to 6 moles per mole of adrenaline.

7. The process according to claims 1 or 2 wherein said persulfate is present in the range 2.0 to 2.5 mole per mole of adrenaline.

8. The process according to claims 1 or 2 wherein the product adrenochrome is stabilized by reaction with a hydrazine compound.

9. The process according to claim 8 wherein said hydrazine compound is selected from the group consisting of semicarbazide and aminoguanidine.

* * * * *

UNITED STATES PATENT AND TRADEMARK OFFICE
CERTIFICATE OF CORRECTION

PATENT NO. : 4,501,923

DATED : February 26, 1985

INVENTOR(S) : Deryck F. Boot

It is certified that error appears in the above-identified patent and that said Letters Patent is hereby corrected as shown below:

[73] Assignee: "Minnesota Mining and Manufacturing Company, St. Paul, Minn." should read [73] Assignee: --Riker Laboratories, Inc., St. Paul, Minn.--

Signed and Sealed this

Seventh Day of January 1986

[SEAL]

Attest:

Attesting Officer

DONALD J. QUIGG

Commissioner of Patents and Trademarks